US008348936B2

(12) United States Patent
Trembly et al.

(10) Patent No.: US 8,348,936 B2
(45) Date of Patent: Jan. 8, 2013

(54) THERMAL TREATMENT SYSTEMS WITH ACOUSTIC MONITORING, AND ASSOCIATED METHODS

(75) Inventors: B. Stuart Trembly, Hanover, NH (US); Jason M. Dahlstrom, White River Junction, VT (US)

(73) Assignee: The Trustees of Dartmouth College, Hanover, NH (US)

( * ) Notice: Subject to any disclaimer, the term of this patent is extended or adjusted under 35 U.S.C. 154(b) by 1469 days.

(21) Appl. No.: 11/932,821

(22) Filed: Oct. 31, 2007

(65) Prior Publication Data

US 2008/0114428 A1 May 15, 2008

Related U.S. Application Data

(63) Continuation-in-part of application No. 11/688,146, filed on Mar. 19, 2007, now Pat. No. 7,713,268, which is a continuation-in-part of application No. 10/730,327, filed on Dec. 8, 2003, now Pat. No. 7,192,429, which is a continuation-in-part of application No. 10/314,670, filed on Dec. 9, 2002, now Pat. No. 7,377,917.

(60) Provisional application No. 60/915,560, filed on May 2, 2007.

(51) Int. Cl.
*A61B 18/18* (2006.01)
(52) U.S. Cl. ............................................. 606/41; 606/33
(58) Field of Classification Search ................... 606/4, 5, 606/23, 27–34, 37, 38, 41, 42; 607/96–104, 607/115
See application file for complete search history.

(56) References Cited

U.S. PATENT DOCUMENTS

| 1,108,686 | A | 8/1914 | Bonis |
| 1,364,148 | A | 1/1921 | Springer |
| 2,126,070 | A | 4/1938 | Wappler |
| 2,347,915 | A | 5/1944 | Landauer |
| 2,525,381 | A | 10/1950 | Tower |
| 3,237,623 | A | 3/1966 | Gordon |
| 3,307,533 | A | 3/1967 | Meredith et al. |
| 3,948,269 | A | 4/1976 | Zimmer |
| 3,978,864 | A | 9/1976 | Smith et al. |
| 3,991,770 | A | 11/1976 | LeVeen |
| 4,003,383 | A | 1/1977 | Bruck |
| 4,014,333 | A | 3/1977 | McIntyre |
| 4,030,480 | A | 6/1977 | Meyer |

(Continued)

FOREIGN PATENT DOCUMENTS

EP 0422112 B1 4/1991

(Continued)

OTHER PUBLICATIONS

Office Action issued in related U.S. Appl. No. 11/688,146, dated Jul. 9, 2009, 4 pages.

(Continued)

*Primary Examiner* — Ahmed Farah
(74) *Attorney, Agent, or Firm* — Lathrop & Gage LLP

(57) ABSTRACT

A thermal treatment system with acoustic monitoring applies substantially constant electromagnetic energy superposed with pulsed electromagnetic energy to targeted tissue. The pulsed electromagnetic energy reacts with tissue to create an acoustic pressure wave within the tissue. The acoustic pressure wave is sensed by an acoustic sensor, and a sensor signal indicative of the acoustic pressure wave is generated and processed to determine changes in tissue composition.

21 Claims, 4 Drawing Sheets

U.S. PATENT DOCUMENTS

| | | | |
|---|---|---|---|
| 4,140,130 A | 2/1979 | Storm, III | |
| 4,326,529 A | 4/1982 | Doss et al. | |
| 4,381,007 A | 4/1983 | Doss | |
| 4,528,991 A | 7/1985 | Dittmar et al. | |
| 4,881,543 A | 11/1989 | Trembly et al. | |
| 5,196,006 A * | 3/1993 | Klopotek et al. | 606/32 |
| 5,263,951 A | 11/1993 | Spears et al. | |
| 5,368,590 A | 11/1994 | Itoh | |
| 5,437,658 A | 8/1995 | Muller et al. | |
| 5,458,596 A | 10/1995 | Lax et al. | |
| 5,641,357 A | 6/1997 | Yamada et al. | |
| 5,749,871 A | 5/1998 | Hood et al. | |
| 5,779,696 A | 7/1998 | Berry et al. | |
| 5,948,011 A | 9/1999 | Knowlton | |
| 6,024,095 A | 2/2000 | Stanley, III | |
| 6,053,909 A * | 4/2000 | Shadduck | 606/3 |
| 6,104,942 A | 8/2000 | Kruger | |
| 6,149,620 A | 11/2000 | Baker et al. | |
| 6,149,643 A | 11/2000 | Herekar et al. | |
| 6,159,205 A | 12/2000 | Herekar et al. | |
| 6,224,593 B1 | 5/2001 | Ryan et al. | |
| 6,364,875 B1 | 4/2002 | Stanley, III | |
| 6,413,255 B1 | 7/2002 | Stern | |
| 6,461,354 B1 | 10/2002 | Olsen et al. | |
| 6,482,201 B1 | 11/2002 | Olsen et al. | |
| 6,485,486 B1 | 11/2002 | Trembly et al. | |
| 6,491,688 B1 | 12/2002 | Lin et al. | |
| 6,520,956 B1 | 2/2003 | Huang | |
| 6,567,688 B1 | 5/2003 | Wang | |
| 6,623,454 B1 | 9/2003 | Eggers et al. | |
| 6,673,069 B1 | 1/2004 | Hood | |
| 6,694,173 B1 | 2/2004 | Bende et al. | |
| 6,773,431 B2 | 8/2004 | Eggers et al. | |
| 6,890,332 B2 | 5/2005 | Truckai et al. | |
| 6,939,344 B2 | 9/2005 | Kreindel | |
| 7,044,945 B2 | 5/2006 | Sand | |
| 7,192,429 B2 | 3/2007 | Trembly | |
| 7,377,917 B2 * | 5/2008 | Trembly | 606/32 |
| 7,899,520 B2 * | 3/2011 | Lian et al. | 600/509 |
| 2002/0002369 A1 | 1/2002 | Hood | |
| 2002/0042612 A1 | 4/2002 | Hood et al. | |
| 2002/0099363 A1 | 7/2002 | Woodward et al. | |
| 2002/0143322 A1 | 10/2002 | Haghighi | |
| 2002/0173777 A1 | 11/2002 | Sand | |
| 2003/0028228 A1 | 2/2003 | Sand | |
| 2003/0163178 A1 | 8/2003 | Davison et al. | |
| 2003/0174281 A1 | 9/2003 | Herekar et al. | |
| 2003/0181899 A1 | 9/2003 | Hood et al. | |
| 2003/0181903 A1 | 9/2003 | Hood et al. | |
| 2004/0111086 A1 | 6/2004 | Trembly | |
| 2005/0107692 A1 | 5/2005 | Li et al. | |
| 2005/0197657 A1 | 9/2005 | Goth et al. | |
| 2005/0245949 A1 | 11/2005 | Goth et al. | |
| 2007/0161976 A1 | 7/2007 | Trembly | |

FOREIGN PATENT DOCUMENTS

| | | |
|---|---|---|
| EP | 0422112 B1 | 2/1996 |

OTHER PUBLICATIONS

Response to Office Action issued in related U.S. Appl. No. 11/688,146, filed Aug. 28, 2009, 3 pages.

Office Action issued in related U.S. Appl. No. 11/688,146, dated Jan. 8, 2009, 7 pages.

Response to Office Action issued in related U.S. Appl. No. 11/688,146, dated Apr. 8, 2009, 7 pages.

Trembly, B.S.; Hashizume, N.; and Moodie, K.S.; "Microwave Thermal Keratoplasty for Myopia: Keratoscopic Evaluation in Porcine Eyes" Journal of Refractive Surgery, pp. 682-688, 2001.

J.C. Lin, On Microwave-Induced Hearing Sensation. IEEE Transactions on Microwave Theory and Techniques. MTT-25 (1977) pp. 605-613.

G. Ku; L.V. Wang, Combining Microwave and Ultrasound: Scanning Thermoacoustic Tomography. Proceedings of the 22nd Annual EMBS International Conference, Jul. 2000, Chicago, IL.

Selected File History from related U.S. Appl. No. 11/688,146, filed Mar. 19, 2007.

Selected File History from related U.S. Appl. No. 10/730,327, filed Dec. 8, 2003.

Selected File History from related U.S. Appl. No. 10/314,670, filed Dec. 9, 2002.

International Search Report issued Jun. 11, 2004 in related PCT Application Serial No. PCT/US03/38978.

International Preliminary Examination Report issued Mar. 22, 2005 in related PCT Application Serial No. PCT/US03/38978.

EP Rule 109 and 110 Communication issued Aug. 5, 2005 in related European Application No. 03796799.9.

Response to EP Rule 109 and 110 Communication issued Aug. 5, 2005 in related European Application No. 03796799.9 filed Sep. 9, 2005.

* cited by examiner

THERMAL TREATMENT SYSTEMS WITH ACOUSTIC MONITORING, AND ASSOCIATED METHODS

RELATED APPLICATIONS

This application claims priority to U.S. Provisional Patent Application Ser. No. 60/915,560, filed May 2, 2007. This application is also a continuation-in-part of U.S. patent application Ser. No. 11/688,146, filed Mar. 19, 2007, which was a continuation of patent application Ser. No. 10/730,327, filed Dec. 8, 2003, now U.S. Pat. No. 7,192,429, which was a continuation-in-part of U.S. patent application Ser. No. 10/314,670, filed Dec. 9, 2002. Each of the above applications and patents is incorporated by reference herein.

BACKGROUND

Thermal treatment systems are used, for example, to ablate liver metastatic tumors, treat benign prostatic hyperplasia, ablate cardiac tissue for the prevention of arrhythmia, heat corneal tissue to correct myopia, occlude the Fallopian tubes and for other therapeutic purposes.

Conventional thermal treatment systems and methods apply constant, or substantially constant, electromagnetic energy until a therapeutic combination of tissue temperature and accumulated treatment time is attained. However, relatively few conventional systems have the ability to monitor progress of a thermal procedure in real-time. It is thus difficult to determine when an intended outcome has been achieved or, more importantly, to regulate energy output in anticipation of an intended outcome, to prevent overshooting of an endpoint.

Minimally-invasive and non-invasive thermal treatment modalities are advantageous because they reduce the risk of infection and decrease recovery times. However, the benefits of non-invasive treatment modalities can only be recognized when monitoring is also performed non-invasively. Some current systems with the ability to non-invasively monitor thermal tissue changes utilize optical techniques, such as near infrared tomography or birefringence techniques. For example, optical opacity or birefringence of corneal tissue may be monitored during a thermal keratoplasty operation to detect the sudden onset of collagen shrinkage that occurs around 60° C. Nonoptical techniques, including electrical impedance imaging and permittivity imaging, may also be used to non-invasively monitor changes in tissue. However, near infrared tomography, electrical impedance imaging and permittivity imaging require several seconds or minutes to create an image, which is typically too long for real-time monitoring of tissue treatments.

In addition to optical and electrical changes, absorption of electromagnetic energy by tissue causes a number of other phenomena. For example, molecules that absorb electromagnetic energy may experience increased rotation and/or vibration. Such energy may dissipate as heat into surrounding tissue where it can cause expansion of liquid in the tissue, and contribute to the formation of an acoustic pressure wave that propagates away from an affected region.

In U.S. Pat. No. 6,694,173, Bende et al. disclose use of acoustic pressure waves to monitor progress of a laser photoablation procedure. The pressure wave is induced by the ablating laser, and differences between tissue layers are detected and stratographically mapped as the tissue layers are ablated. Thus, the '173 patent monitors tissue removal rather than compositional changes within a given target tissue.

SUMMARY

The present instrumentalities advance the art by providing thermal treatment systems incorporating means for acoustically sensing thermally-induced changes in tissue composition.

In an embodiment, a thermal treatment system with acoustic monitoring, for inducing changes in tissue composition, includes a first pair of electrically conductive elements for applying substantially constant electromagnetic energy to the tissue to achieve a therapeutic effect. A second pair of electrically conductive elements provides pulses of electromagnetic energy superposed over the substantially constant electromagnetic energy. A sensor detects an acoustic pressure wave produced by the tissue in response to the pulsed electromagnetic energy, and transmits a sensor signal representative of the acoustic pressure wave. A processor receives the sensor signal and determines the changes in tissue composition.

In an embodiment, an improvement in a system including an applicator used for thermally inducing a change in tissue composition includes a sensor configured to detect an acoustic pressure wave. The acoustic pressure wave is produced by the tissue in response to pulsed electromagnetic energy superposed over substantially constant electromagnetic energy. The sensor provides a sensor signal representative of the acoustic pressure wave. A feedback system adapted to receive the sensor signal and analyze the sensor signal determines when a treatment modality has achieved an intended effect.

In an embodiment, a method of thermally-inducing a change in tissue composition includes generating substantially constant electromagnetic energy and superposing pulsed electromagnetic energy over the substantially constant electromagnetic energy to generate an acoustic pressure wave. The generated acoustic pressure wave is sensed, to provide a corresponding acoustic signal. The acoustic signal is processed to determine the change in tissue composition.

In an embodiment, a thermal treatment system with acoustic monitoring, for inducing changes in tissue composition, includes an apparatus for applying electromagnetic energy to the tissue to achieve a therapeutic effect. The electromagnetic energy has a substantially constant component and a pulsed component. A sensor detects an acoustic pressure wave produced by the tissue in response to the pulsed component of the electromagnetic energy, and transmits a sensor signal representative of the acoustic pressure wave. A processor receives the sensor signal and determines the changes in tissue composition.

DETAILED DESCRIPTION

As used herein, "compositional changes" or "changes in tissue composition" refer to macroscopic chemical and/or physical changes that occur within a given target tissue. Compositional changes include, but are not limited to, temperature induced expansion or contraction, dessication, rupture of cell membranes, protein folding or unfolding, and the like.

As used herein, "constant" or "substantially constant" energy has a time-averaged value of power that is effective for elevating tissue temperature to a therapeutic level where a change in tissue composition occurs. In one example of "constant" or "substantially constant" energy, a signal having a 100% duty cycle provides a steady level of output sufficient to raise temperature of tissue to a point where tissue composition is altered. In another example of "constant" or "substantially constant" energy, a signal having a duty cycle of less than 100% (i.e., a time-varying signal) may provide a sufficiently large time-averaged value of power to elevate tissue temperature to a therapeutic level. As an example, a signal having a 50% duty cycle that provides 20 watts of power during the "on phase", and 0 watts of power during the "off phase", has a time-averaged value of 10 watts, which is sufficient to elevate temperature of some tissue types to a point where tissue composition is altered. The energy of the signal having a 50% duty cycle may therefore be considered "constant" or "substantially constant" energy for tissues that are compositionally altered by 10 watts of power. "Constant" or "substantially constant" energy may thus be applied to tissue as intermittent or modulated power so long as a sufficiently large time-averaged value of power is provided to elevate tissue temperature to a therapeutic level.

As used herein, "pulsed" energy is delivered as short bursts of power, where the time-averaged value of the power is insufficient for elevating tissue temperature to a therapeutic level. Instead, pulsed energy is used to produce an acoustic pressure wave that interrogates tissue without substantially altering tissue composition.

Figure 1:
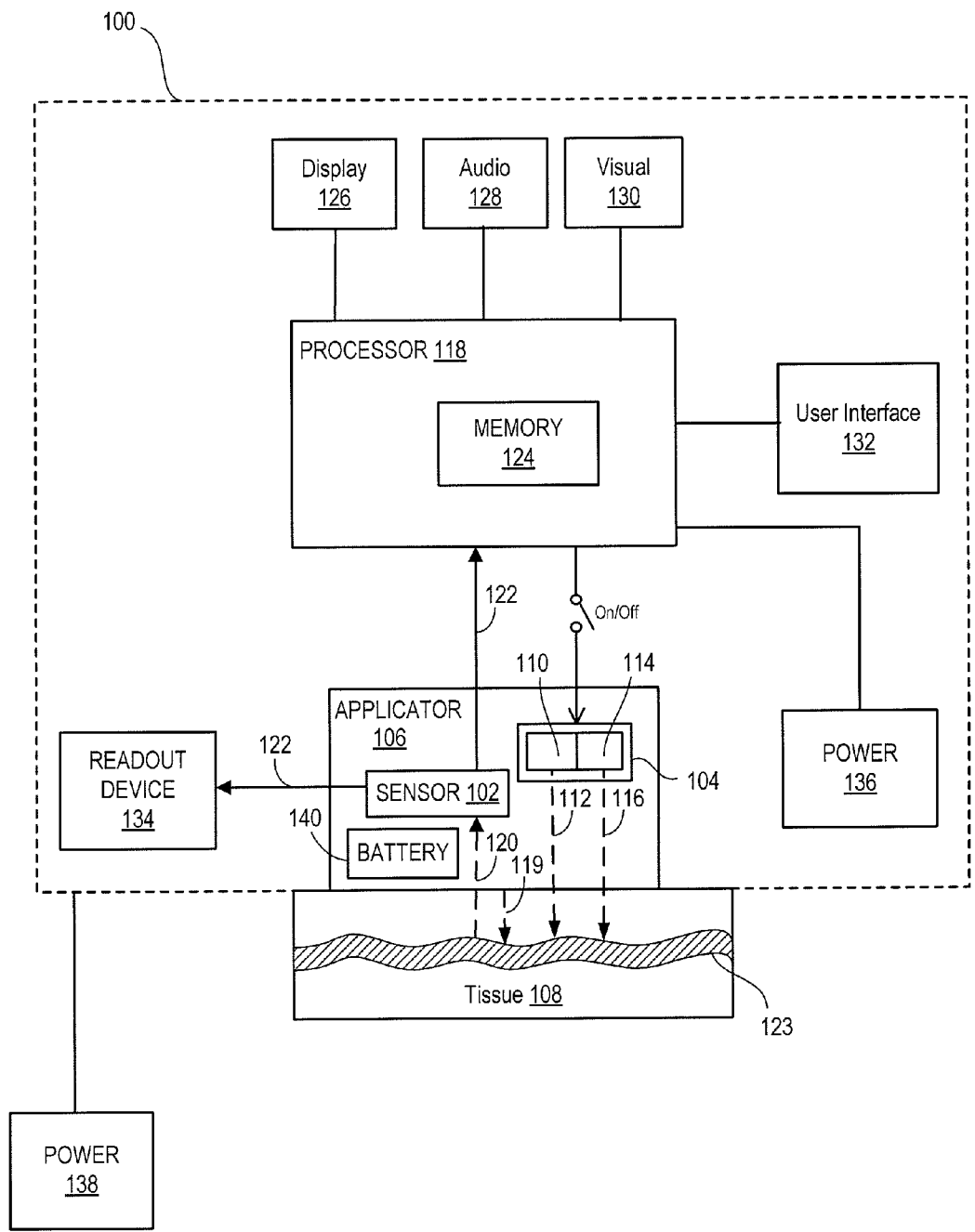
FIG. 1 is a block diagram of a thermal treatment system with acoustic monitoring, configured for operation in a reflective mode, according to an embodiment.

FIG. 1 schematically shows an exemplary thermal treatment system 100 for thermally inducing changes in tissue. System 100 (shown bounded by a dashed line, for ease of illustration) includes an acoustic sensor 102 and an energy source 104 for producing electromagnetic energy. Source 104 is for example included within an applicator 106 that delivers the electromagnetic energy to tissue 108. Acoustic sensor 102 is likewise shown within applicator 106, near source 104. However, sensor 102 may optionally be outside of applicator 106. For example, as in the transmissive applications described below, one or more sensors may be remote from applicator 106. Multiple remote sensors may for example monitor uniformity of tissue heating.

In one embodiment, source 104 includes at least one first element 110 for generating substantially constant electromagnetic energy 112, and at least one second element 114 for generating pulses of electromagnetic energy 116. For example, element 110 may be a pair of electrically conductive elements for applying substantially constant electromagnetic energy 112 to tissue 108. Element 114 may likewise be a pair of electrically conductive elements that generates pulses of electromagnetic energy 116.

In another embodiment, a single element (e.g., first element 110 or second element 114) may alone produce a signal that has both a substantially constant component 112 and a pulsed component 116. It will be appreciated that such a waveform may be produced by intensity modulation methods known in the art.

In another embodiment, a single electrically conductive element (e.g., a horn antenna) may deliver both the substantially constant electromagnetic energy and the pulsed electromagnetic energy.

Pulsed electromagnetic energy 116 superposed over substantially constant electromagnetic energy 112 (or an equivalent waveform) is delivered to tissue 108 via applicator 106. Pulsed energy 116 may be of greater magnitude than substantially constant energy 112. Such an impulsive waveform is known to produce acoustic energy 119 due to sudden, local thermal expansion of tissue (J. C. Lin, "On Microwave-Induced Hearing Sensation," *IEEE Transaction on Microwave Theory and Techniques*, MTT-25: 605-613, 1977). Acoustic sensor 102 detects reflected acoustic energy or a pressure wave, depicted as line 120 (also referred to as acoustic energy 120 or acoustic wave 120), and generates a sensor signal 122 corresponding to the frequency and/or magnitude of received acoustic energy 120. As used herein, the term "acoustic" refers not only to sound waves within the audible range for humans, e.g., between about 20-20,000 Hz, but also to frequencies above and below this range. For example, mechanical energy of vibration having infrasonic and ultrasonic frequencies also fall within the scope of the present systems and methods.

Processor 118 receives sensor signal 122 and monitors changes therein to detect changes in heated tissue, in real-time. Processor 118 controls applicator 106 (for example by controlling on/off status of applicator 106 and/or output of source 104) to achieve a desired treatment effect. In one reflective mode, acoustic energy 119 propagates away from the point of origin (i.e., tissue proximal to applicator 106), then reflects from a tissue boundary 123 created as an effect of heating by substantially constant energy 112. Reflected acoustic energy 120 is detected by sensor 102, which is for example an acoustic transducer, such as a piezoresistive or piezoelectric device that is oriented to quantify parameters including tissue pressure. Detection of reflected acoustic energy, where there was previously none, indicates that electromagnetic heating has modified tissue 108.

In one example, tissue 108 is liver tissue. Thermally-ablated liver tissue may have different acoustic properties than normal liver tissue, due to desiccation or tissue contraction. The discontinuity of acoustic properties at boundary 123 of the ablated liver tissue 108 causes a partial or full reflection of acoustic energy 119, as is known in wave theory. In another example, tissue 108 is corneal tissue. When the cornea of the eye is heated to about 60° C., corneal collagen shrinks, with a consequent change in its water content, density, and other properties. These changes are also likely to cause acoustic reflection. Controlled corneal shrinkage is used to change the shape and focusing ability of the eye. Thus, the detection of acoustic energy 120 reflected from the zone of shrinkage (e.g., tissue boundary 123) may signal that the treatment effect has been attained and that power to source 104 can be turned off.

In the examples cited, surface cooling may be employed at the point of contact between applicator 106 and tissue 108. A cooling system may be configured to cool the applicator, during an operation, by flowing coolant at the interface between applicator 106 and tissue 108. In another example, the cooling system may comprise a Peltier or thermoelectric cooling device or a system for circulating liquid coolant in upper regions of the applicator, but not bottom regions proximate the bottom surface of the applicator. Exemplary surface cooling is described in commonly-owned, copending U.S. Pat. No. 7,192,429 and in commonly-owned, copending U.S. patent application Ser. Nos. 10/314,670 and 11/688,146.

Consequently, the maximum temperature and the region of tissue effect (e.g., tissue boundary 123) are located at depth within the body. In this case, system 100 operates in a range-finding mode, using the transmitted pulsed electromagnetic energy 116 and the reflected acoustic energy 120 to detect a treatment effect or compositional change at a displaced location. This mode may eliminate the need to place invasive thermometry sensors within the patient's body, as is often done in conventional practice. Because the reflected acoustic energy or pressure wave 120 and corresponding sensor signal 122 can be used to turn off power to source 104 almost instantly, safety and efficacy of surface or deep thermal treatment are improved over conventional systems.

In one embodiment, a feedback circuit is adapted to receive and analyze sensor signal 122 to determine when a treatment modality has achieved an intended effect. Sensor signal 122 communicates information concerning electromagnetic energy applied to tissue, such as reflected energy, transmitted energy, and acoustic energy received from tissue.

In one aspect, processor 118 monitors received sensor signal 122 and/or changes in sensor signal 122, for example, comparing a level of or degree of change in signal 122 to pre-set values indicative of various treatment levels or effects. Such pre-set values may be stored in a memory 124. When a desired change in sensor signal 122 is detected, e.g., a reflected acoustic signal is detected, indicating thermal treatment at tissue boundary 123, processor 118 may automatically stop application of substantially constant and pulsed electromagnetic energy 112, 116.

Processor 118 may monitor sensor signal 122 and, through a feedback loop, vary the level of substantially constant electromagnetic energy 112 applied and/or adjust the temperature of a cooling device as treatment approaches completion. For example, processor 118 may compare strength of sensor signal 122 or changes in sensor signal 122 to a pre-set value indicative of a desired level of tissue tightening/collagen contraction of skin tissue in a cosmetic application. As received sensor signal 122 approaches a desired value, processor 118 may reduce the magnitude of substantially constant electromagnetic energy 112 to avoid overshooting the desired level of tissue tightening. As described above, once the desired strength or change in sensor signal 122 is detected, processor 118 may stop application of substantially constant and pulsed electromagnetic energy 112, 116.

In one embodiment, processor 118 communicates output indicative of treatment progress to one or more of a display 126, an audio indicator 128 and a visual indicator 130. Display 126 may be a screen or monitor that shows a visual representation of treatment progress, e.g., a real-time graph showing treatment progress, a countdown to completion of treatment, etc. Audio indicator 128 is, for example, a bell, buzzer, beeper, tone generator or alarm that sounds upon completion of treatment stages, or when a desired treatment effect is achieved. Audio indicator 128 may likewise sound to indicate that treatment is nearing the desired effect. Visual indicator 130 may be a light or series of lights indicating completion of treatment, completion of treatment stages, or impending completion of treatment (e.g., the approach of a desired treatment effect).

A user interface 132, such as a keyboard, touch-screen, series of buttons or other input, facilitates manual control of system 100. A medical practitioner, for example, enters values corresponding to a desired level of treatment for a particular patient. Processor 118 translates the entered values to corresponding sensor signal strengths and/or acceptable levels of substantially constant and pulsed electromagnetic energy 112, 116 applied by applicator 106, e.g., using information and algorithms in memory 124. The practitioner-entered values may likewise be stored in memory 124, e.g., in a patient-specific file.

The practitioner may override automatic control of system 100 using user interface 132 to stop, start and adjust transmission of substantially constant electromagnetic energy 112 and/or pulsed electromagnetic energy 116. In one aspect, pulsed electromagnetic energy 116 is automatically adjusted by processor 118 as a function of the level of substantially constant electromagnetic energy 112 selected by the practitioner. The magnitude of pulsed energy 116 is, for example, set sufficiently above the background heating power (provided by substantially constant energy 112), to produce acoustic energy 119.

Acoustic sensor 102 may be a sensing device suitable for capturing and detecting acoustic energy propagating away from thermally treated tissue 108. Generally, a transducer that converts pressure waves into mechanical energy and/or electrical energy may be used in the present systems. As discussed above, sensor 102 may be a piezoelectric or piezoresistive device in contact with tissue 108.

In another embodiment, sensor 102 may be a non-contact sensor. In one example, at least one microphone may be used as a transducer that changes a sound wave into an electrical signal. A particularly effective non-contact transducer is a capacitor microphone where one of the plates is suitably flexible and responsive to changing air pressure. The changing air pressure in the acoustic pressure wave causes one plate of the capacitor to move back and forth. Because capacitance C across the plates is inversely proportional to the separation of the plates, the pressure wave can cause the capacitance to change. This, in turn, causes the charge Q on the plates to change (C=QV) so that an electric current is generated at the same frequencies as the striking pressure wave. To increase the electric signal generated by the capacitor microphone, an amplifier may be positioned between the microphone and oscilloscope or processor to amplify the signal output from the sensing microphone (e.g., sensor 102).

The electric current generated by the microphone transducer, having the same frequencies as the acoustic pressure waves, may be sent to both processor 118 and a separate readout device 134. The readout device may include an x-y recorder, e.g., video display terminals, plotters and the like. In alternative embodiments, the readout device may include either an oscilloscope, a microprocessor or a combination of both to provide an acoustic signal output representation such as a frequency plot. The acoustic signal output is mathematically manipulated to generate a representative pattern of a specific tissue composition.

System 100 may include at least one internal power source 136, such as a battery for powering processor 118 and/or associated components (e.g., display 126, audio indicator 128, visual indicator 130 and user interface 132), for example, in the event of a power outage. Readout device 134 may share power source 136 (connections not shown, for clarity) or readout device 134 may be powered by a separate battery (also not shown). Additionally, one or more components of system 100 may connect to an outside power source 138. Applicator 106 may be connected with processor 118 via one or more wires, and may thus share power source 136, or applicator 106 may wirelessly communicate with processor 118 and be powered by external power source 138 and/or an internal battery 140.

Figure 2:
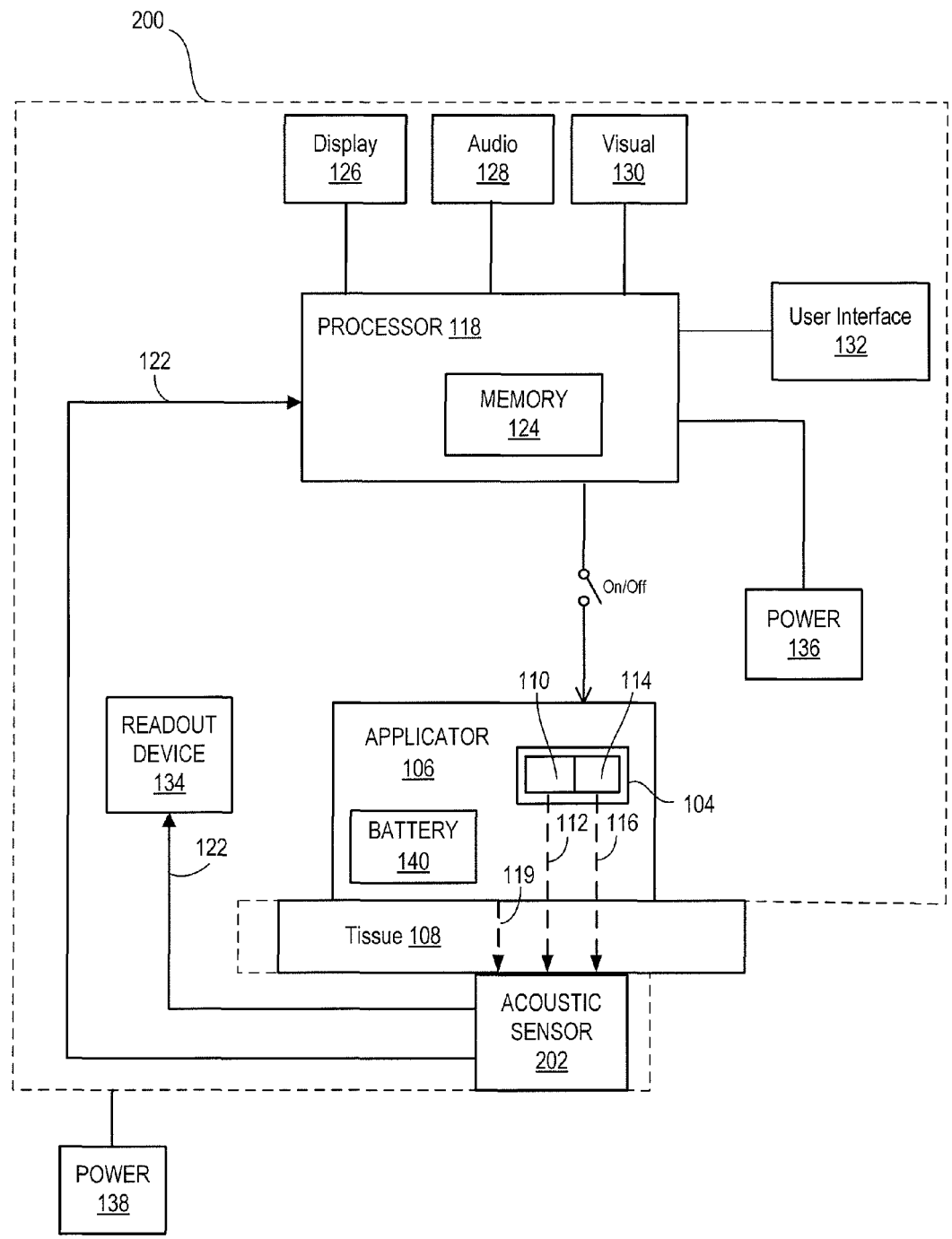
FIG. 2 is a block diagram of a thermal treatment system with acoustic monitoring, configured for operation in a transmissive mode, according to an embodiment.

FIG. 2 depicts a thermal treatment system 200 employing an acoustic sensor 202 disposed remotely from applicator 106 for operation in a transmissive mode. It will be understood that components of systems 100 and 200 may be interchangeable. For ease of explanation, features common to systems 100 and 200 are identified by reference numbers used above with respect to FIG. 1.

Acoustic energy 119 propagates from a point of origin (e.g., tissue 108 subjected to pulsed and substantially constant electromagnetic energy 112, 116) toward remote acoustic sensor 202 to form a transmission system, instead of the reflection system of FIG. 1. Here, repeated pulses of acoustic energy 119 will change their magnitude or time of flight if tissue properties change with temperature along the transmission path. In this mode, reflection of energy by a region of thermally-modified tissue (e.g., boundary 123) is not required. Rather, system 200 detects subtle changes associated with increasing temperature along the acoustic transmission path. For example, a phase-locked loop may be established before electromagnetic power is applied. After application of substantially constant and pulsed electromagnetic energy 112, 116, the control effort required to maintain the phase-locked loop may be a sensitive measure of changing tissue properties as tissue temperature increases. System 200 may thus be useful in controlling a treatment in which gross changes, such as desiccation or collagen shrinkage, are not produced.

In one embodiment, multiple remote acoustic sensors 202 may be used at separate locations to detect uniformity of tissue heating. Multiple sources and sensors may also be used to measure relative pre-treatment locations of electromagnetic sources in tissue 108. For example, uniformity of spacing of radio-frequency needles that may be inserted into a patient's liver, to ablate tumor tissue, may be measured.

System 100/200 may employ non-metallic acoustic sensors 102/202 to avoid interference with substantially constant and pulsed electromagnetic energy 112, 116. Examples of non-metallic acoustic sensors include fiber optic cable configured to detect motion or pressure of tissue placed in contact therewith through interferometry, and modified for matching of acoustic impedance. Fiber optic acoustic sensors 102/202 may be manufactured in a variety of sizes to meet the desired application for system 100/200. For example, very compact (<1 mm diameter) fiber optic cables fit within many small devices conventionally used to apply electromagnetic power, such as interstitial electromagnetic antennas that are inserted into tissue.

Figure 3:
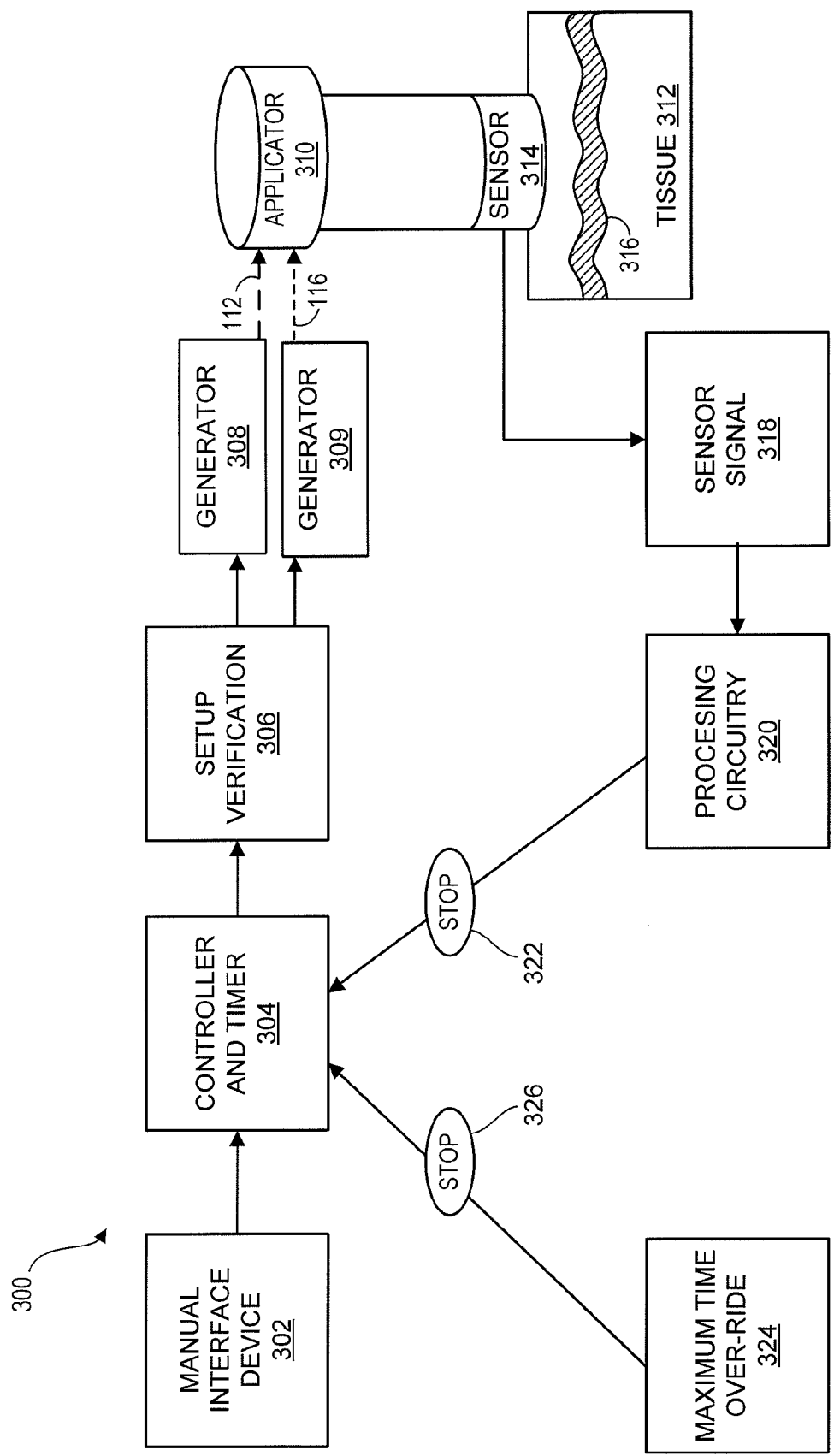
FIG. 3 is a block diagram illustrating treatment of tissue with the thermal treatment system of FIG. 1 or FIG. 2.

FIG. 3 is a block diagram depicting tissue treatment with a thermal treatment system 300 incorporating an acoustic sensor 314. System 300 may utilize components of either system 100 or system 200. In operation, system 300 senses a physical variable in target tissue 312 by monitoring reflected or transmitted acoustic energy propagating from a treatment area when electromagnetic energy is applied. System 300 additionally provides sensed feedback affecting a thermal treatment modality. A physician or other medical worker manually accesses an interface device 302, such as a computer keyboard or touch screen, that facilitates the selection and/or initiation of a treatment modality. The interface device 302 may request manual input, such as depth of target tissue, parameters of applied electromagnetic energy (for example, wavelength and/or intensity of energy), maximum treatment time, selection of a treatment modality by specific selection or class of modality, and/or goals for adjusted physical variables obtainable as a result of treatment (e.g., a degree of occlusion or tissue tightening).

A programmable controller 304 accepts program instructions that optionally access user input data or program selections from the interface device 302 and causes system 300 to implement a selected thermal treatment modality. Setup verification 306 may be a user-interactive operation that verifies the modality and assures that system 300 is correctly positioned or configured for the intended thermal treatment. Once setup is verified, a generator, such as microwave or other electrical signal generator 308, produces a level of substantially constant electromagnetic energy 112 required for the intended thermal treatment. A second generator 309 produces pulses of electromagnetic energy 116 having a magnitude that is greater than the magnitude of substantially constant electromagnetic energy 112, and supplies this energy to an applicator 310. In an embodiment, substantially constant energy 112 is a near-microwave emission of 915 MHz (approved by the FCC for medical use), to reduce system cost; however, generator 308 may be operated at other conventionally used frequencies, such as 2450 MHz, that are understood to have therapeutic benefits according to a desired modality. Alternatively, either generator 308 or 309 may produce a signal having both a substantially constant component 112 and a pulsed component 116, as described above. Applicator 310 applies substantially constant and pulsed energy 112, 116 to target tissue 312 to induce the desired thermal effect.

Electrical energy useful in the present invention includes radiant electromagnetic energy at frequencies from about 100 MHz to 30 GHz. Thermal treatment systems typically utilize electromagnetic energy having frequencies permitted by the Federal Communications Commission (FCC) for industrial, scientific or medical use (ISM frequencies). In the United States, the most common ISM bands are 902-928 MHz and 2.4-2.4835 GHz. Most treatment modalities operating in the 902-928 MHz range are referred to as "microwave" treatments, even though such emissions are slightly below the 1 GHz cutoff that many persons use to identify the microwave band. "Radio frequency" treatments may describe energetic treatment by excitation at lower frequencies. Microwave and radio frequency treatments may be used to achieve similar results, but the applied energy affects tissue in different ways according to the various wave properties. For example, radio frequency electromagnetic energy has a larger resistive heating component than microwave frequency energy. As used herein, the term "microwave" is intended to encompass radiant electromagnetic energy oscillating at frequencies ranging from about 100 MHz to about 30 GHz, more preferably from about 500 MHz to about 3000 MHz.

Returning to FIG. 3, target tissue 312 may inherently have differing physical properties, or variables that may be affected in different ways by electromagnetic (e.g., microwave or radio frequency) energy and the consequent temperature elevation. For example, a tumor or hyperplasic area may differ in composition, density, water content or other characteristics from a healthy tissue area; thus, the diseased and healthy areas may react differently to both substantially constant and pulsed energy. Different layers of tissue, e.g., the epidermis, dermis and subcutis of the skin, and underlying fat and muscle, may likewise have differing physical variables and thus differing reactions to substantially constant and pulsed energy 112, 116. Acoustic energy generated by thermal expansion of treated tissue in response to pulsed energy 116 is therefore variable according to the physical variables of target tissue 312.

An acoustic sensor 314 senses reflected acoustic energy created by heating of tissue 312 and provides a sensor signal 318 that embodies a direct or indirect measurement of the physical variables. Processing circuitry 320 receives signal 318 and analyzes the same to determine if and when the modality has achieved a desired treatment effect. Processing circuitry 320 may generate a stop signal 322 that terminates treatment when the physical variable has been modified to within a predetermined range or value. Sensor 314 may be one or more of the sensors described above, such as:

a fiber optic sensor;
a thin film or microelectronic thermal transducer;

a mechanical transducer, such as a piezoresistive or piezoelectric device;

or a force-sensitive quartz resonator.

In one embodiment, a safety mechanism is built into program instructions for controller 304 as a clock-based maximum time over-ride 324 that generates a stop signal 326 at the termination of a safe time interval for the selected modality. This feature may help to assure that operation of generator 308, 309 does not exceed a specified amount of time at any given level of output and is intended to avoid unintended thermal damage to tissue 312. Most types of microwave or radio frequency applicators may be used generally in the aforementioned system 300, provided the applicator is fitted with acoustic sensor 314.

Where system 300 operates in reflective mode, substantially constant and pulsed energy 112, 116 are applied to tissue 312. Substantially constant energy 112 acts upon tissue 312 to thermally create a boundary 316 of treated tissue at a location remote from applicator 310 due to the action of surface cooling. Acoustic sensor 314 senses reflected acoustic energy created by heating of tissue 312 and provides a sensor signal 318 indicative of the reflected acoustic energy. Processing circuitry 320 receives and analyzes signal 318 to determine the presence of reflected acoustic energy and thus, the establishment of boundary 316, which indicates that tissue 312 has been modified. Processing circuitry 320 may generate stop signal 322 upon detection of reflected acoustic energy.

Though not shown in FIG. 3, where system 300 operates in transmissive mode, acoustic sensor 314 may be remote from applicator 310. As physical variables of tissue 312 change with temperature, acoustic waves propagating from treated tissue 312 change in magnitude and/or time of flight. Sensor 314 detects these changes and generates sensor signal 318 indicative of changes in received acoustic energy. Processing circuitry 320 processes sensor signal 318 and varies application of energy 112, 116 via controller and timer 304 in response to detected changes in tissue composition, indicated by changes in sensor signal 318. Processing circuitry 320 may stop treatment via stop signal 322 when acoustic energy correlating to a desired thermal treatment effect is sensed at sensor 314, for example when tissue 312 has been modified to within a predetermined range or value.

Figure 4:
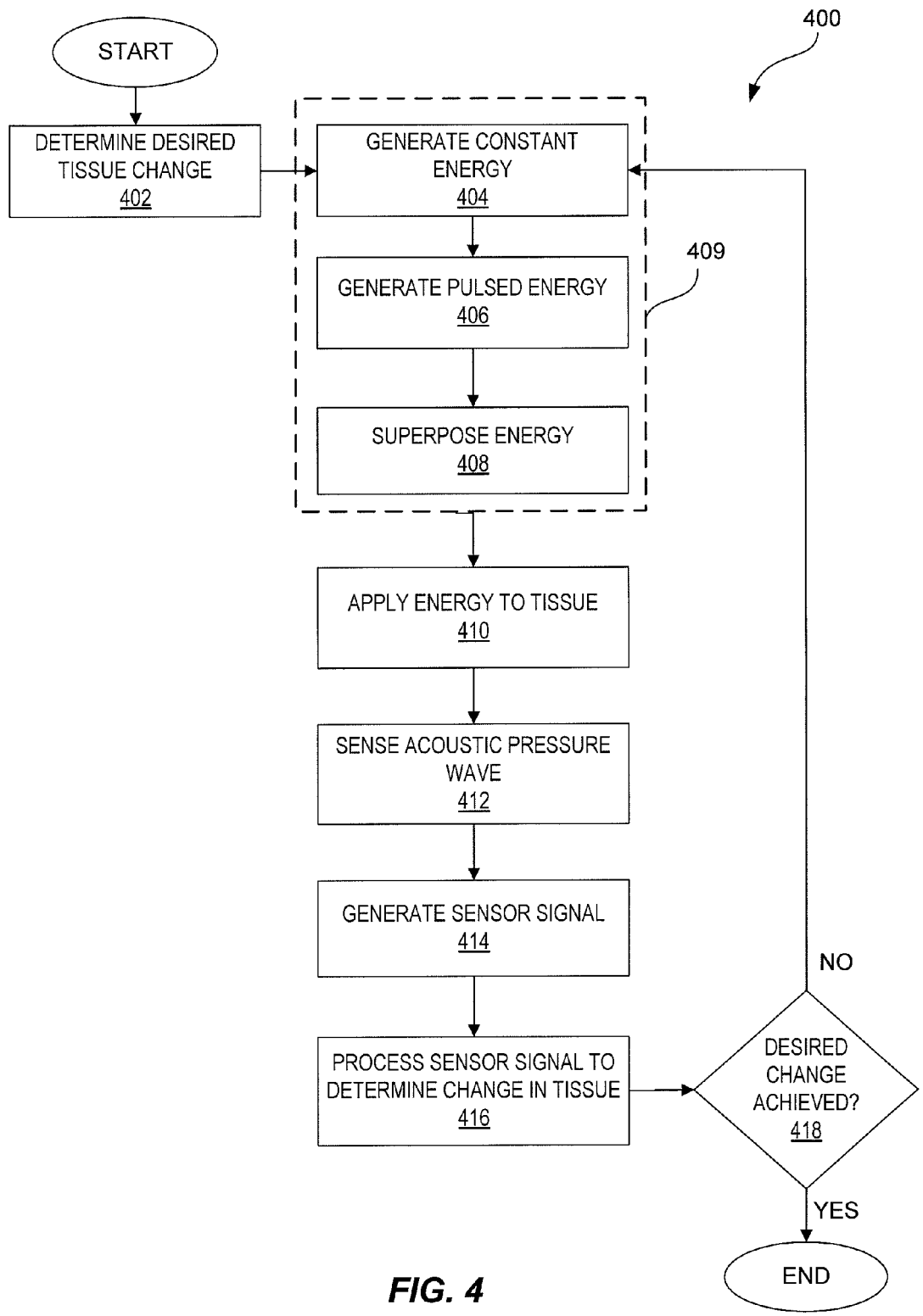
FIG. 4 is a flowchart showing one exemplary method for treating tissue using a thermal treatment system with acoustic monitoring.

FIG. 4 is a flowchart depicting a method 400 of treating tissue with a thermal treatment system with acoustic monitoring. Method 400 for example includes applying microwave, radio frequency or other heat transmitting energy, sensing a physical variable in tissue as the tissue is affected by a thermal treatment operation to provide a sensor signal representative of the physical variable, receiving the sensor signal, and analyzing the sensor signal to determine when a treatment modality has achieved an intended effect.

A desired change in target tissue is determined in step 402. In one example of step 402, a physician provides processor 118 with treatment parameters via user interface 132. Alternately, the physician may select a treatment modality or therapeutic application, such as corneal remodeling, a degree of collagen contraction, dessication, cell membrane rupture, structural occlusion, etc., and processor 118 may call up treatment parameters associated with the modality, e.g., from memory 124 (FIGS. 1 and 2).

In steps 404 and 406, substantially constant and pulsed electromagnetic energy are generated. Pulsed electromagnetic energy is superposed over substantially constant electromagnetic energy in step 408. Steps 404-408 may occur substantially simultaneously, as indicated by dotted box 409. In one example of steps 404-408, source 104 (or element 110) generates substantially constant electromagnetic energy 112 in the microwave range, while source 104 (or element 114) generates pulses of electromagnetic energy 116 at an increased magnitude as compared with substantially constant energy 112. Pulsed energy 116 is superposed over substantially constant energy 112 (see FIGS. 1 and 2). In another embodiment, source 104 (element 110 or 114) generates intensity modulated energy having a pulsed component 116 superposed upon a substantially constant component 112.

In step 410, pulsed energy is applied to target tissue. An acoustic pressure wave is sensed in step 412, and a corresponding sensor signal generated in step 414. In an example of steps 410-414, energy is applied to target tissue 108 (FIGS. 1 and 2). Pulsed energy 116 produces acoustic energy 119 within tissue 108, e.g., due to thermal expansion. Acoustic sensor 102 senses transmitted acoustic energy 119 and generates a sensor signal 122 representative of acoustic energy 119. In another example of steps 410-414, substantially constant energy 112 thermally modifies tissue 108 composition, e.g., inducing localized desiccation or shrinkage to create a tissue boundary, such as boundary 123 (FIG. 1). Acoustic energy 119 reflects from tissue boundary 123, and acoustic sensor 102 senses reflected acoustic energy 120 and generates a sensor signal 122 indicative of the received acoustic energy 120.

In step 416, the sensor signal is processed to determine a change in the target tissue. In an example of step 416, changes in sensor signal 122 are monitored to determine real-time compositional changes in tissue 108, for example as substantially constant energy 112 acts upon a given tissue layer, e.g., creating tissue boundary 123. Step 418 is a decision. If the desired change has been achieved, method 400 ends. If the desired change has not been achieved, method 400 continues with steps 404-418. In an example of steps 416-418, processor 118 receives and processes sensor signal 122 and determines, according to variations in sensor signal 122, that tissue boundary 123 has been created. This determination may signify that tissue 108 has been sufficiently modified, and method 400 may end. It will be appreciated that manual over-ride may be initiated at any point in method 400, so that a physician or clinician administering thermal treatment may end or modify treatment, e.g., according to patient response.

In another example of steps 416-418, processor 118 processes received sensor signal 122 to monitor subtle changes in tissue 108. Changes in magnitude or interval between acoustic energy pulses 120 originating from tissue 108 are communicated via variations in sensor signal 122 to processor 118. Processor 118 compares sensor signal 122 to values indicative of the desired tissue change, and controls application of substantially constant and pulsed electromagnetic energy 112, 116 to reach, but not overshoot, the desired change. Sensing step 412 may involve one or more acoustic sensors, e.g., sensors 102 that are remote from applicator 106, to monitor uniformity of treatment.

When utilizing systems 100-300 or operating a thermal treatment system with acoustic monitoring, for example, according to method 400, modulation frequency may be automatically adjusted by processor 118 or manually adjusted via user interface 132. Modulation frequency is typically adjusted to a value that is different from any natural environmental oscillation that might interfere with the analysis, and more preferably, to a frequency that maximizes the intensity of the signal measured, such as an acoustically resonant frequency. Determining the acoustic resonant frequency and the corresponding appropriate wavelength may be calculated by known methods and equations within the skill of the art. Generally, any energy source that produces electromagnetic energy in the visible, infrared and/or ultraviolet spectrum may be used. Generally, modulation frequencies range from about 1 Hz to about 100 MHz, and often from about 500 Hz to about 500 kHz.

Since certain changes may be made in the above systems and methods without departing from the scope hereof, it is intended that all matter contained in the above description or shown in the accompanying drawings be interpreted as illustrative, and not in a limiting sense. For example, according to various instrumentalities and embodiments herein, at least one additional sensor may be used to provide an additional sensor signal. The feedback circuitry may be configured to process the sensor signals in combination to determine when the treatment modality has achieved the intended effect as a function of the respective signals. It is also to be understood that the following claims are to cover generic and specific features described herein, and all statements of the scope of the invention which, as a matter of language, might be said to fall there between.

What is claimed is:

1. A thermal treatment system with acoustic monitoring for inducing changes in tissue composition, comprising:
a first pair of electrically conductive elements for applying substantially constant electromagnetic energy to the tissue to achieve a therapeutic effect;
a second pair of electrically conductive elements for providing pulses of electromagnetic energy superposed over the substantially constant electromagnetic energy;
a sensor for detecting an acoustic pressure wave produced by the tissue in response to the pulsed electromagnetic energy and for transmitting a sensor signal representative of the acoustic pressure wave; and
a processor for receiving the sensor signal and for determining the changes in tissue composition.

2. The system of claim 1, wherein the processor adjusts the substantially constant electromagnetic energy based on the determined changes in tissue composition.

3. The system of claim 1, further comprising a generator for applying an electrical signal having a selected frequency across the first pair of electrically conductive elements.

4. The system of claim 3, wherein the processor is coupled to the generator for applying control signals thereto.

5. The system of claim 4, wherein the control signals cause any of initiating a treatment protocol or terminating a treatment protocol.

6. The system of claim 3, wherein the processor applies a stop signal to the generator when a treatment time associated with a treatment protocol exceeds a threshold defined for a treatment modality.

7. The system of claim 3, wherein the selected frequency is in a range between 902 MHz and 928 MHz.

8. The system of claim 1, further comprising a generator for applying an electrical signal having a selected frequency across the second pair of electrically conductive elements, the selected frequency being in a range between 2.4 GHz and 2.4835 GHz.

9. The system of claim 1, wherein the sensor is a transducer, and the transducer is selected from a capacitor microphone, a piezoelectric device, a piezoresistive device, a thermal transducer, a force-sensitive quartz resonator and a fiber optic interferometer.

10. The system of claim 1, further comprising at least one additional sensor that provides an additional sensor signal, and the processor being configured to process the sensor signal and the additional sensor signal, in combination, to determine the changes in tissue composition.

11. A method of thermally-inducing a change in tissue composition, comprising:
generating substantially constant electromagnetic energy;
superposing pulsed electromagnetic energy over the substantially constant electromagnetic energy to generate an acoustic pressure wave;
sensing the generated acoustic pressure wave to provide a corresponding acoustic signal; and
processing the acoustic signal to determine the change in tissue composition.

12. The method of claim 11, wherein the generated acoustic pressure wave is sensed by a transducer, and the transducer is selected from a capacitor microphone, a piezoelectric device, a piezoresistive device, a thermal transducer, a force-sensitive quartz resonator and a fiber optic interferometer.

13. The method of claim 11, wherein the substantially constant electromagnetic energy has a frequency in a range between 902 MHz and 928 MHz.

14. The method of claim 11, wherein the pulsed electromagnetic energy has a frequency in a range between 2.4 GHz and 2.4835 GHz.

15. The method of claim 11, further comprising adjusting the substantially constant electromagnetic energy according to the change in tissue composition.

16. A thermal treatment system with acoustic monitoring for inducing changes in composition of tissue, comprising:
an apparatus for applying electromagnetic energy to the tissue to achieve a therapeutic effect, the electromagnetic energy having a substantially constant component and a pulsed component;
a sensor for detecting an acoustic pressure wave produced by the tissue in response to the pulsed component of the electromagnetic energy and for transmitting a sensor signal representative of the acoustic pressure wave; and
a processor for receiving the sensor signal and for determining the changes in composition of tissue.

17. The system of claim 16, wherein the processor adjusts the substantially constant component based on the determined changes in tissue composition.

18. The system of claim 16, wherein the processor is coupled to a generator for applying control signals thereto and the control signals cause any of initiating a treatment protocol or terminating a treatment protocol.

19. The system of claim 18, wherein the processor applies a stop signal to the generator when a treatment time associated with a treatment protocol exceeds a threshold defined for the treatment modality.

20. The system of claim 16, wherein the sensor is a transducer, the transducer is selected from a capacitor microphone, a piezoelectric device, a piezoresistive device, a thermal transducer, a force-sensitive quartz resonator and a fiber optic interferometer.

21. The system of claim 16, further comprising at least one additional sensor that provides an additional sensor signal, the processor being configured to process the sensor signal and the additional sensor signal, in combination, to determine the changes in tissue composition.

* * * * *